United States Patent [19]

Wong

[11] Patent Number: 5,026,992
[45] Date of Patent: Jun. 25, 1991

[54] SPECTRAL RATIOING TECHNIQUE FOR NDIR GAS ANALYSIS USING A DIFFERENTIAL TEMPERATURE SOURCE

[75] Inventor: Jacob Y. Wong, Santa Barbara, Calif.
[73] Assignee: Gaztech Corporation, Goleta, Calif.
[21] Appl. No.: 403,587
[22] Filed: Sep. 6, 1989
[51] Int. Cl.⁵ .............................. G01J 5/12; G01J 5/58
[52] U.S. Cl. ..................................... 250/343; 250/339; 250/352
[58] Field of Search ........................ 250/343, 339, 352

[56] References Cited

U.S. PATENT DOCUMENTS

| | | | |
|---|---|---|---|
| 3,793,525 | 4/1974 | Burch et al. | 250/343 |
| 3,811,776 | 6/1974 | Blau, Jr. | 250/343 X |
| 4,233,513 | 11/1980 | Elder et al. | 250/343 |
| 4,499,379 | 2/1985 | Miyatake et al. | 250/352 |
| 4,500,207 | 2/1985 | Maiden | 250/343 X |
| 4,501,968 | 2/1985 | Ebi et al. | 250/352 X |
| 4,567,366 | 1/1986 | Shinohara | 250/339 |
| 4,578,762 | 3/1986 | Wong | 544/177 |
| 4,605,313 | 8/1986 | Kebabian | 250/343 X |
| 4,605,855 | 8/1986 | Kumada et al. | 250/231 |
| 4,647,777 | 3/1987 | Meyer | 250/339 |
| 4,662,755 | 5/1987 | Aoki et al. | 356/414 |
| 4,694,173 | 9/1987 | Wong | 250/343 |
| 4,709,150 | 11/1987 | Burough et al. | 250/338.1 |

FOREIGN PATENT DOCUMENTS 8903028  4/1989  World Int. Prop. O. ......... 250/339

Primary Examiner—Constantine Hannaher
Assistant Examiner—Jacob M. Eisenberg
Attorney, Agent, or Firm—Daniel C. McKown

[57] ABSTRACT

An instrument for determining the concentration of a particular gas that might be present in a sample has no moving parts and is extremely compact. The instrument uses as a source of radiation a device that has a radiating element whose temperature is alternated between $T_1$ and $T_2$ and whose spectrum approximates that of a blackbody. Radiation from this source is passed through a dual pass band filter that has two non-overlapping pass bands, one of which is centered at a wavelength at which the gas absorbs and the other of which is centered at a wavelength at which the sample does not absorb radiation. After passing through this filter, the radiation passes through the sample chamber and then is intercepted by a detector which produces an electrical signal determined by the radiation intercepted. The electrical signal is processed to provide an indication of the concentration of the gas.

6 Claims, 3 Drawing Sheets

SPECTRAL RATIOING TECHNIQUE FOR NDIR GAS ANALYSIS USING A DIFFERENTIAL TEMPERATURE SOURCE

BACKGROUND OF THE INVENTION

1. Field of the Invention

The present invention is in the field of non-dispersive infrared (NDIR) gas analyzers of a type typically used to measure the concentrations of unwanted or combustible gases so that an alarm can be given when their concentration approaches a harmful or dangerous level. More specifically, the present invention relates to a comparatively small apparatus having no moving parts and capable of measuring the concentration of one or more specified components in a mixture of gases.

2. The Prior Art

The NDIR technique utilizing the characteristic absorption bands of gases in the infrared has been widely used in the gas analyzer industry for the detection of these gases. Such gas analyzers utilize the principle that various gases exhibit substantial absorption at specific wavelengths in the infrared radiation spectrum. The term "non-dispersive" as used herein refers to the apparatus used, typically a narrow-band optical or infrared transmission filter instead of a dispersive element such as a prism or diffraction grating, for isolating for purposes of measurement the radiation in a particular wavelength band that normally coincides with a strong absorption band in the absorption spectrum of a gas to be measured. The NDIR technique offers a number of distinct advantages over previous methods that use the principle of heat transfer based upon radiation absorption by certain gases. These advantages include speed of response, measurement stability, greater sensitivity and simpler implementation.

Over the years a large number of measurement techniques based upon the NDIR principle for the detection of have been proposed and successfully demonstrated. In one such gas analyzer shown and described in U.S. Pat. No. 3,793,525 by Burch, et al., a beam of infrared energy emanates from an infrared source and passes through a sample chamber containing an unknown gas mixture. Before reaching an infrared detector, the beam is passed through one or more narrow band-pass filters, which may be mounted on a filter wheel. Typically, each filter only passes radiation at the characteristic absorption wavelength of a particular gas of interest. Another filter may also be used as a reference filter at a wavelength close to, but not overlapping, the characteristic absorption wavelength of any of the gases present in the sample cell. This type of gas analyzer requires the generation of some type of synchronizing signal in order to coordinate the operation of the signal processing circuit with the rotation of the filter wheel.

Another type of NDIR gas analyzer is shown and described in U.S. Pat. No. 3,811,776 by Blau, Jr. It incorporates (in addition to the infrared source, sample chamber, narrow band-pass filter and detector) a reference cell (a gas cell containing the gas of interest, e.g., $CO_2$) and an identical cell evacuated or filled with a gas that is transparent at the wavelength used (4.26 microns for $CO_2$) such as $N_2$. These two cells alternately are moved into and out of the radiation beam. Since a sample chamber is placed in series with these cells, the alternate introduction of the absorbing and nonabsorbing cells into the radiation beam creates, respectively, a reference detector signal and a sample detector signal whose ratio is used to determine the gas concentration in the sample chamber. Unlike the configuration described in U.S. Pat. No. 3,793,525 alluded to earlier, which utilizes two interposed optical filters to create a sample and reference detector signal, the Blau configuration takes advantage of the principle of nonlinear absorption by the gas to be measured (as discussed in U.S. Pat. No. 4,578,762 by Wong) in order to create the reference and sample signals.

Another improved type of such gas analyzer is shown and described in U.S. Pat. No. 4,694,173 by Wong. This gas analyzer has no moving parts for effecting either the interposition of optical filters or absorbing and nonabsorbing cells to create both a sample and a reference detector signal as in the NDIR gas analyzers described earlier.

All of the NDIR gas analyzers described above for the measurement of the concentrations of one or more gases in a mixture perform well functionally and have contributed overwhelmingly to the overall technical advancement in the field of gas analysis during the past two decades. They are widely accepted in both the medical and industrial communities. Despite their undisputed success over the years, there remain quite a number of applications, primarily in the industrial sector, where these NDIR techniques are still too complex, and hence too costly, to be taken advantage of. One such example is the methane gas detector for the miners. The ideal solution here is a small, very low cost and battery-operated methane gas sensor mountable directly below the headlight on the miner's helmet. In the event the miner encounters a methane gas pocket during excavation in the mine, this particular sensor can detect a dangerous level of the gas much sooner than the current setup in which a relatively bulky methane analyzer is normally located many feet behind the working miners. Furthermore, such a helmet-mounted methane gas sensor allows the alarm to be placed inside the helmet and close to the miner's ears thereby avoiding the tragic possibility that the alarm from a more remote methane analyzer might be drowned out by the machine noises in the mine.

Another example is the commonplace household fire sensor. Fire sensors in use today in almost all public buildings and private dwellings are in essence smoke detectors as they only detect the smoke resulting from a fire. These sensors are compact and low cost, but they have been known to generate frequent and annoying false alarms. It is generally believed that the detection of an elevated level of carbon dioxide gas as a result of the combustion process taking place in any fire is a better alternative to the smoke detector in terms of false alarms. However, implementation of such a fire sensor using NDIR techniques presently available is far too complex and costly to serve as a viable alternative.

In view of these situations and the incessant drive for better and lower cost gas analyzers, new techniques are constantly being proposed and introduced all aiming at coming up with still better solutions. Maiden in U.S. Pat. No. 4,500,207 and Wong in U.S. Pat. No. 4,694,173 proposed NDIR techniques for gas detection without any moving parts such as mechanical choppers. The goal was to render NDIR sensors solid-state and hence more rugged and compact for use in a host of new applications.

Yamada in U.S. Pat. No. 4,605,855 further proposed an NDIR gas analyzer with a compact cell structure but retaining a mechanical chopper.

Kebabian in U.S. Pat. No. 4,605,313 proposed a new approach using an absorptive film on the surface of a thermal detector as a means to detect gases of interest. The behavior of the absorptive film specific only to the gas of interest directly modifies the detector output thus creating a unique signal. The reference is derived by using a chopper to detect a gas which does not affect the behavior of the absorptive film, thus generating a different signal at the same detector.

Even more recently Aoki in U.S. Pat. No. 4,662,755 disclosed the design of an NDIR gas analyzer with means for varying the angle of incidence of light on an interference filter in order to effect a reference and a sample path at two different wavelengths. Unfortunately, a mechanical chopper is again needed for implementing this particular design.

Despite these recent disclosures of new and simpler NDIR techniques for gas measurements, the goal of devising a uniquely simple device of small size and low cost, battery-operable, and with no moving parts has not been achieved until the presently disclosed invention.

The present inventor takes advantage of recent technological advances in infrared components. One area is the infrared source. The latest available device in this area is the so-called electrically modulatable infrared microsource which is, in essence, a small thick film resistor pad made out of special material capable of being heated and cooled at relatively high rate (up to 100 Hz, typically). This is achieved via standard $I^2R$ pulsing using a square voltage waveform. Infrared micro-sources composed of a thick film of resistive material are available from Dynatech Electro-Optics Corporation of San Luis Obispo, Calif., and from Novametrix of Seattle, Wash. Micro-sources using a heated filament are available from Chicago Miniature Lamp Works of Chicago, Ill., and from Gilway Technical Lamp Co. of Woburn, Mass.

Another area of infrared components where recent technological advances make a significant impact is in narrow bandpass filters. Today not only can one make an excellent narrow bandpass filter with one center wavelength or pass band, filters with two narrow passbands centered at two spectrally separated wavelengths can also be routinely manufactured. Such a dual passband filter also plays a crucial part in the present invention. Dual pass band infrared filters are available from Barr Associates of Westford, Mass. and from OCLI of Santa Rosa, Calif.

SUMMARY OF THE INVENTION

It is an object of the present invention to advance a novel NDIR technique so simplified that small, solid state, very low-cost and battery-operated gas sensors can be constructed to meet a host of special applications hitherto impossible using presently available NDIR techniques primarily because of the relative complexity and high cost.

It is a further object of the present invention to provide an improved apparatus for the measurement of gases using the novel NDIR technique herein disclosed.

In accordance with a preferred embodiment, the present invention uses a differential temperature source capable of alternating between two stable emission temperatures $T_1$ and $T_2$ where it is assumed that $T_2 > T_1$. Such an operating condition is achieved by pulsing the source with two periodic square voltage waveforms having amplitudes $V_1$ and $V_2$ with $V_2 > V_1$, where $V_1$ and $V_2$ correspond to source temperatures $T_1$ and $T_2$ respectively. The source emits under these conditions radiations of two different spectral contents according to Planck's radiation law, namely $e(T_1) \cdot R_{bbL}(T_1)$ and $e(T_2) \cdot R_{bbL}(T_2)$ where $e(T)$ is the emissivity function of the source at temperature T and $R_{bbL}(T)$ is the spectral radiant emittance function at temperature T. Since the infrared source in question behaves very much like a blackbody, we therefore assume that $e(T_1) = e(T_2) = 1$ and rewrite the source outputs at $T_1$ and $T_2$ as $R_{bbL}(T_1)$ and $R_{bbL}(T_2)$ respectively. It is well known that the spectral output of a blackbody source is also governed by the Wien's displacement law which states that $$L_m \cdot T = \text{constant} = 2,897.8 \text{ micron} - °K.$$

where $L_m$ is the wavelength measured in microns at which the maximum spectral radiant emittance occurs and T is the source temperature in °K. Thus the wavelength at which the peak spectral radiant emittance occurs for source temperature $T_2$, namely $L_m(T_2)$ is shorter than the corresponding $L_m(T_1)$ at source temperature $T_1$ since $T_2 > T_1$.

If we now interpose a dual pass-band interference filter in front of the differential temperature source with the pass-bands located at $L_1$ and $L_2$ respectively such that $L_2 > L_1$, the radiation emanating from the filter will further be modified by the latter according to the spectral positions of the two pass-bands and the source temperature T. For source temperatures $T_1$ and $T_2$ the spectral radiation output after the dual pass-band filter is respectively $R_{bbL}(T_1) \cdot [F(L_1) + F(L_2)]$ and $R_{bbL}(T_2) \cdot [F(L_1) + F(L_2)]$ where $F(L)$ is the spectral transmission function for the pass-band filter at center wavelength L. The gas measurement system is completed by placing in line after the dual pass-band filter a sample chamber followed by an infrared detector.

Suppose we now make $L_2$ coincide spectrally with the absorption band of a gas whose concentration we wish to measure and $L_1$ spectrally at a position where no appreciable absorption takes place for all the commonly encountered gases including the one to be measured and further define a spectral ratio $R_s$ to be $$R_s = A \cdot R_{bbL}((T_1) \cdot [F(L_1) + F(L_2)] / R_{bbL}(T_2) \cdot [F(L_1) + F(L_2)]$$

where A is a constant accounting for the detector spectral responsivity and the overall transmission efficiency of the measurement system. The spectral ratio $R_s$ can be written as $$R_s = A \cdot [B_1(T_1, L_1) + C_1(T_1, L_2)] / [B_2(T_2, L_1) + C_2(T_2, L_2)]$$

where A, $B_1(T_1, L_1)$ and $B_2(T_2, L_1)$ are constants at a given source temperature pair $(T_1, T_2)$ independent of the amount of the gas of interest present in the sample chamber and $C_1(T_1, L_2)$ and $C_2(T_2, L_2)$ vary with the amount of the gas in question in the sample chamber. The manner in which the two C functions vary with the amount of gas present in the sample chamber depends strongly upon the choice of the source differential temperatures $T_1$ and $T_2$. Thus the spectral ratio $R_s$ defined above can be used to correlate the amount of gas present in the sample chamber which has an absorption band at wavelength $L_2$ provided that the reference wavelength $L_1$ is properly chosen and the temperature pair $(T_1,T_2)$ of the differential temperature source is correctly optimized for maximum signal.

Thus, the preferred embodiment of the present invention comprises a differential temperature infrared source followed by a dual pass-band interference filter, a sample chamber and an infrared detector. One of the pass-bands of the filter coincides with a suitable absorption band of the gas to be measured and the other pass-band is chosen to lie at a spectral position where there is no appreciable absorption by any of the commonly encountered gases, including the one to be measured. The operating temperatures of the differential temperature infrared source are individually optimized for the particular gas to be measured.

The novel features which are believed to be characteristic of the invention, both as to organization and method of operation, together with further objects and advantages thereof, will be better understood from the following description considered in connection with the accompanying drawings in which the preferred embodiment of the invention is illustrated by way of example. It is expressly understood, however, that the drawings are for the purpose of illustration and description only and are not intended as a definition of the limits of the invention.

DETAILED DESCRIPTION OF THE PREFERRED EMBODIMENT

Figure 1:
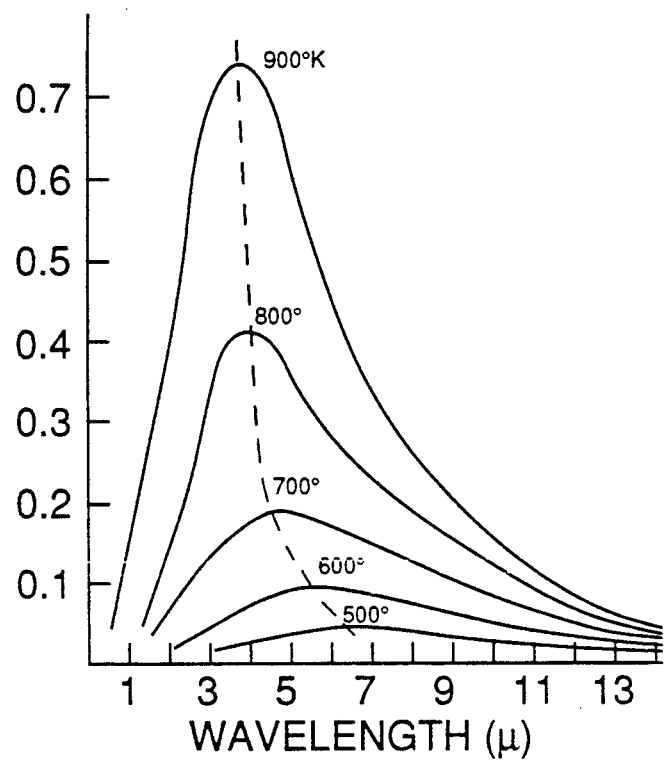
FIG. 1 is a graph showing the spectral radiant emittance of a blackbody at temperatures 500°–900° K.

FIG. 1 shows the spectral radiant emittance of a blackbody source at temperatures T ranging from 500° K. to 900° K. Several characteristics of the radiation from such a blackbody source are evident from these curves. The total radiant emittance, which is proportional to the area under the curves, increases rapidly with temperature. The wavelength of maximum spectral radiant emittance shifts towards shorter wavelengths as the temperature increases. This is commonly referred to as Wien's displacement law as expounded earlier. Furthermore, the individual curves never cross one another; hence the higher the temperature, the higher the spectral radiant emittance at all wavelengths.

Figure 2:
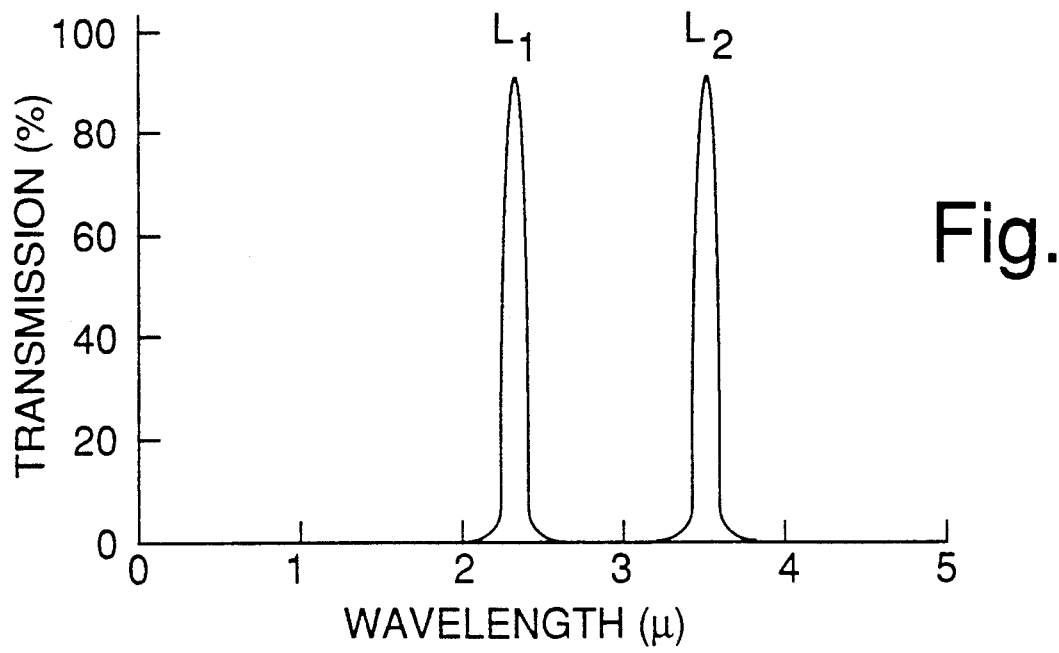
FIG. 2 is a graph showing the spectral transmission curve for a dual pass-band filter used in the preferred embodiment.
Figure 3:
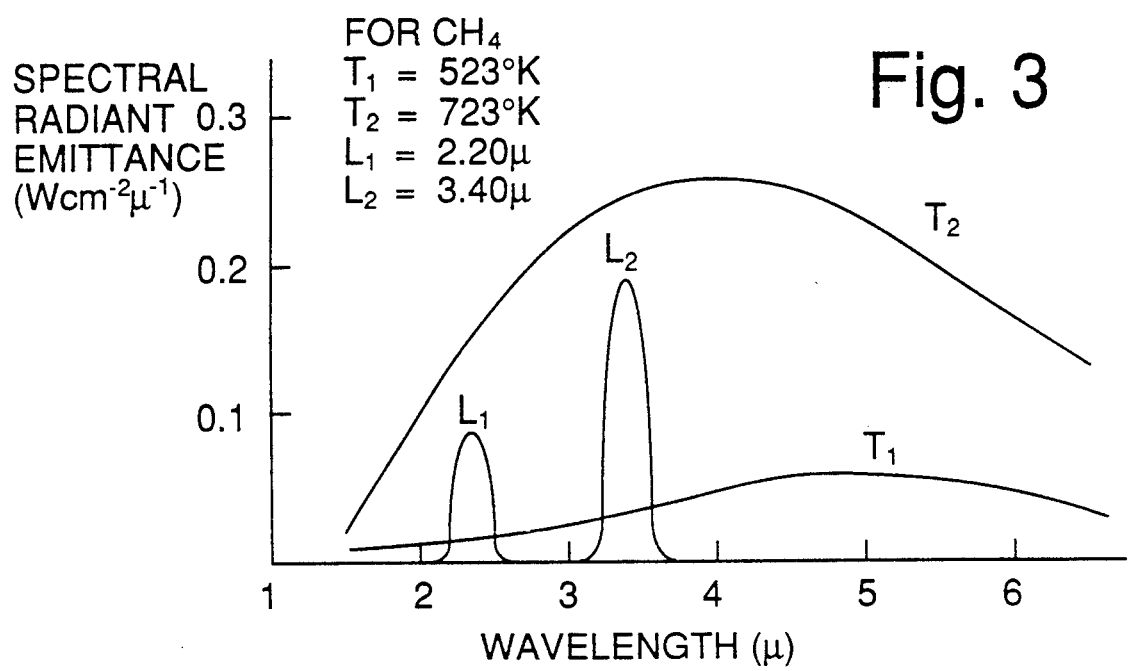
FIG. 3 is a graph showing the spectral radiant emittance of the differential temperature infrared source at the operating temperatures of $T_1$ and $T_2$ convoluted with the spectral transmission curve of the dual bandpass filter of the preferred embodiment.

In most NDIR measurement systems using a blackbody, the infrared source is normally maintained at a constant temperature and thus its spectral radiant emittance is typically represented by one of the curves in FIG. 1 dependent upon its absolute temperature. A differential temperature source as used in the present invention, capable of alternating between two stable temperatures $T_1$ and $T_2$ ($T_2 > T_1$ by assumption), will assume two such curves in FIG. 1. In essence a differential temperature source generates two different spectral radiant emittances at two alternating time intervals by assuming two different temperatures. When a dual pass-band filter having pass bands centered at wavelengths $L_1$ and $L_2$ respectively ($L_2 > L_1$ by assumption) as depicted spectrally in FIG. 2 is placed in front of the differential temperature source, the subsequent outputs emerging from the filter will have been modified by the spectral transmission functions of the filter pass bands. As illustrated in FIG. 3 the amount of radiation at the center wavelengths of the respective pass-bands will change as the differential temperature source alternates between its two temperature states.

Figures 4, 5:
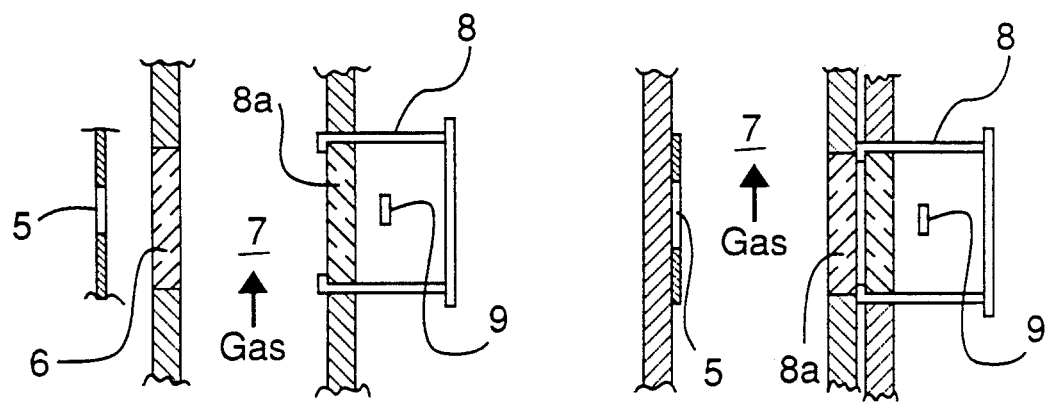
FIG. 4 is a diagram showing the relative positions of the electrical and optical components in a preferred embodiment of the invention.
FIG. 5 is a diagram showing the relative positions of the electrical and optical components in an alternative embodiment of the invention; and, FIG. 6 is an electrical block diagram showing the interconnections of the optical and electronic components in the preferred embodiment of the invention.

With reference to the optical system for the preferred embodiment, as shown in FIG. 4, a dual pass-band filter 6 is placed in front of a differential temperature source 5 so as to intercept a substantial fraction of its Lambertian distributed (blackbody) radiation. In alternative embodiments, lenses and mirrors are used to capture a larger fraction of the radiation and to form it into a beam that passes through the sample chamber. An infrared detector 9 such as a pyroelectric detector or PbSe photoconductor is placed a short distance away on the opposite side of the filter 6 from the source. Such a detector is packaged in a standard TO-5 can 8 whose hermetically sealed window 8a forms together with the filter 6 the sample chamber 7 through which gases of interest to be measured may pass. Since the detector collects a significant portion of the radiation that has passed through the dual pass-band filter, the amount of radiation reaching it can be represented quantitatively as follows:

For source temperature $T_1$:
$A_1 \cdot R_{bbL}(T_1)[F(L_1)+F(L_2)]$

For source temperature $T_2$:
$A_2 \cdot R_{bbL}(T_2)[F(L_1)+F(L_2)]$

The constants $A_1$ and $A_2$ account for the spectral responsivity of the detector and the overall optical efficiency of the system and are independent of temperatures $T_1$ and $T_2$. $R_{bbL}(T)$ is Planck's spectral radiant emittance function at the temperature T in °K. and $F(L)$ is the spectral transmission function of the band-pass filter centered at wavelength L.

In accordance with a preferred embodiment of the invention, a spectral ratio $R_s$ is defined as follows:

$$\begin{aligned}R_s &= A \cdot R_{bbL}(T_1)[F(L_1) + F(L_2)]/ \\ & \quad R_{bbL}(T_2)[F(L_1) + F(L_2)] \\ &= A \cdot [B_1(T_1, L_1) + C_1(T_1, L_2)]/ \\ & \quad [B_2(T_2, L_1) + C_2(T_2, L_2)]\end{aligned}$$

where $B_1(T_1, L_1) = R_{bbL}(T_1) \cdot F(L_1);$
$C_1(T_1, L_2) = R_{bbL}(T_1) \cdot F(L_2);$
$B_2(T_2, L_1) = R_{bbL}(T_2) \cdot F(L_1);$
$C_2(T_2, L_2) = R_{bbL}(T_2) \cdot F(L_2)$ If we now choose the value of $L_2$ to coincide with an appropriate absorption band of a gas selected for measurement and the value of $L_1$ such that there are no appreciable absorptions at that wavelength for all commonly encountered gases including the gas of interest, then the spectral ratio $R_s$ can be used to determine the amount of the gas of interest in the sample chamber of a system, such as that depicted in FIG. 4. The reason is as follows. When there is no gas of interest in the sample chamber the ratio $R_s$ reduces to a value $r.A$ where $r$ is only a function of $T_1$ and $T_2$. Thus, if $T_1$ and $T_2$ are constant, $R_s = r.A = $ constant. Further, when the gas of interest is introduced into the sample chamber, $B_1$ and $B_2$ remain constant as there is no absorption at the wavelength $L_1$, while $C_1$ and $C_2$ will change according to the concentration of the gas in the sample chamber. Furthermore, the amount of change will be different dependent upon whether the differential temperature source is at temperature $T_1$ or $T_2$. Thus $R_s$ can be calibrated to the amount of the gas of interest in the sample chamber for a given set of $T_1$ and $T_2$ used by the differential temperature source.

From the above development it is seen that R is a known function of $T_1$, $T_2$, $L_1$ and $L_2$. Ordinarily the assumption is made that the source has the spectral distribution of a blackbody, which distribution is well known. Alternatively, the actual spectral distribution of the source can be measured in advance by well known techniques. In either case R is a known function of $T_1$, $T_2$, $L_1$ and $L_2$, and this opens up the possibility of optimizing R as a function of the variables, for a particular gas of interest.

Assuming $T_1$ is different from $T_2$ and $L_1$ is different from $L_2$, R is almost certain not to equal 1.00, although theoretically that could result if the blackbody peaks corresponding to $T_1$ and $T_2$ were deliberately chosen to lie at certain specific locations on opposite sides of $L_2$. Barring that exceptional case, R will have a value different from 1.00 and the method of the present invention will be viable.

However, optimization of R with respect to $T_1$, $T_2$, $L_1$ and $L_2$ may be desirable to increase the accuracy of the measurement. The optimization can be carried out by mathematical calculations exclusively, if desired, because the functional relationships are known. Alternatively, the optimization can be carried out experimentally by systematically varying $T_1$, $T_2$, and $L_1$. $L_2$ is chosen to coincide with the chosen absorption band of the gas to be detected or measured. $L_1 < L_2$ and $L_1$ is chosen to coincide with a wavelength at which none of the gases present in the sample chamber absorb. Thereafter, R is calculated for various combinations of T and $T_2$, using the known spectral distributions and the combination yielding the minimum value of R is the combination that is optimum.

Although in the preferred embodiment the concentration of the gas to be detected is inferred from the spectral ratio R as defined above, in other embodiments other variables than R may be used. For example, a difference in the detected radiation levels or a difference in the logarithms of the detected radiation levels are used instead of R in other embodiments. The present invention is concerned with a combination of elements that produce the desired difference in detected radiation levels, and the specific functional relation by which these levels are related to the concentration is incidental, but not trivial.

In an alternative embodiment, the components are arranged as in FIG. 5. Here, the radiation passes through the dual pass band filter 2 after traversing the sample chamber 6. The equations developed above are equally applicable to this embodiment.

Figure 6:
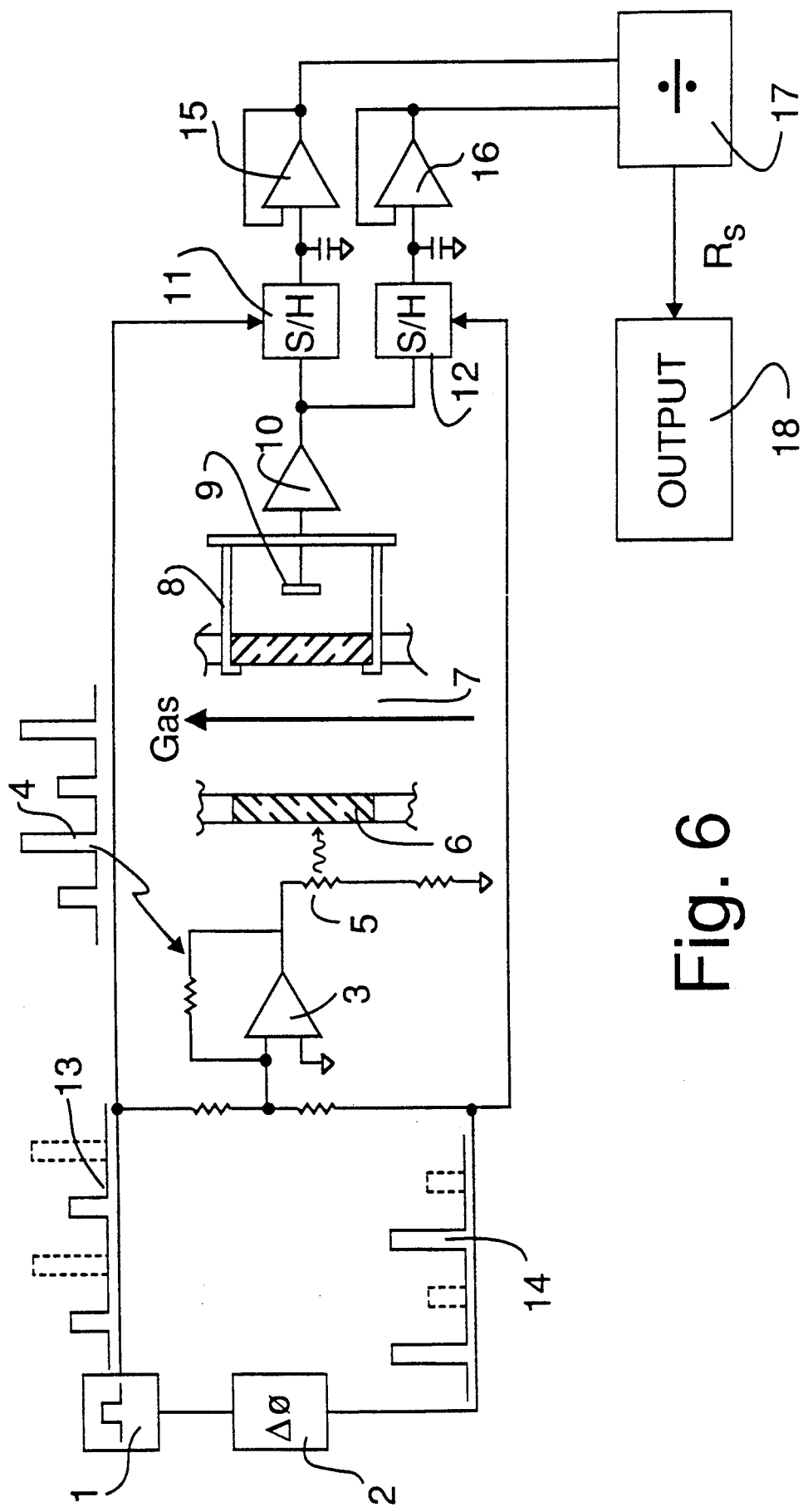

With reference to the block diagram for the optical and electronic elements of the preferred embodiment of the current invention as shown in FIG. 6, a square wave voltage generator 1 is used in conjunction with a phase shifter 2 and amplifier 3 to generate a train of voltage pulses with alternately high and low square voltages. This periodic voltage waveform 4 is applied to infrared source 5 to render it a differential temperature source. Radiation emanating from source 5 passes through the dual pass-band filter 6 which also serves as the entrance window for the sample chamber 7. The exit window of the sample chamber 7 is the hermetically sealed window of a TO-5 can 8 which houses an infrared detector 9.

The detector 9 collects the radiation emerging from the filter 6 after it has passed through the sample chamber 7 and produces a signal in relation to the intensity of the collected radiation. The signal is conditioned by preamplifier 10 before being sampled by two sample-and-hold circuits 11 and 12. S/H circuits 11 and 12 are respectively synchronized and controlled by the two phase-shifted square waveforms 13 and 14 generated by the square wave generator 1 for detecting the peak voltage values corresonding to the two temperature states of the differential temperature source 6. After further amplification by amplifiers 15 and 16, the two voltage values sampled by S/H circuits 11 and 12 are applied to an analog divider circuit 17 to obtain the spectral ratio $R_s$. The output of the analog divider 17 is applied to a display device 18 for calibration and measurement output.

When the preferred embodiment of the present invention is applied to the detection of methane gas, the values for $T_1$, $T_2$, $L_1$, and $L_2$ are optimized to be 523° K., 723° K., 2.20 microns, and 3.40 microns respectively.

Table 1 shows the calculated values of the spectral ratio $R_s$ as a function of methane gas concentration for a sample path length of 6 mm. One can see from Table 1 that the present invention works well for methane gas for the set of system parameters chosen. The present invention works equally well for other gases such as $CO_2$, CO, etc., but each gas requires a different optimized set of system parameters ($T_1$, $T_2$, $L_1$, and $L_2$).

TABLE I

| Methane Concentration (Vol. %) | $R_s$ (Normalized) |
| --- | --- |
| 0 | 1.000 |
| 1 | 1.010 |
| 2 | 1.020 |
| 3 | 1.030 |
| 4 | 1.042 |
| 5 | 1.069 |
| 10 | 1.291 |

Thus, there has been described an instrument for determining the concentration of a particular gas that might be present in a sample. The instrument has no moving parts and is extremely compact and inexpensive. It can be applied to measure any of a number of gases. A key feature of the invention is the combination of a dual pass band filter with a differential temperature source.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. A gas analyzer for determining the concentration of a gas that is included in a sample, comprising in combination:

a sample chamber containing the sample;

differential temperature source means including a radiating element and including means for altering the temperature of said radiating element from $T_1$ to $T_2$ and from $T_2$ to $T_1$ for producing radiation having a first spectrum when the temperature is $T_1$ and having a second spectrum when the temperature is $T_2$;

dual pass band filter means located between the radiating element of said differential temperature source means and said sample chamber, and having two non-overlapping pass bands, one of which is centered at a wavelength at which the gas absorbs radiation and the other of which is centered at a wavelength at which the sample does not absorb radiation, for simultaneously passing radiation within the two nonoverlapping pass bands;

detector means for intercepting radiation that has passed through said dual pass band filter means and through said sample chamber and for converting the intercepted radiation to an electrical signal; and, circuit means electrically connected to said detector means for processing the electrical signal to determine the concentration of the gas;

said sample chamber, said differential temperature source means, said dual pass band filter means, said detector means, and said circuit means all remaining stationary when the gas analyzer is in use.

2. The gas analyzer of claim 1 wherein the gas is methane, wherein one of said two non-overlapping pass bands is centered at a wavelength $L_1 = 2.20$ microns and the other of which is centered at a wavelength $L_2 = 3.40$ microns.

3. In a gas analyzer of the type having a sample chamber containing a sample including a gas whose concentration is to be determined and through which radiation passes to a greater or lesser extent depending on the concentration of the gas, having a detector that intercepts radiation that has passed through the sample of gas and that converts the intercepted radiation to an electrical signal, and having circuit means connected to the detector for processing the electrical signal, the improvement comprising in combination:

differential temperature source means including a radiating element and means for altering the temperature of said radiating element from $T_1$ to $T_2$ and from $T_2$ to $T_1$ for producing radiation having a first spectrum when the temperature is $T_1$ and having a second spectrum when the temperature is $T_2$; and, dual pass band filter means having two nonoverlapping pass bands, one of which is centered at a wavelength at which the gas absorbs radiation and the other of which is centered at a wavelength at which the sample does not absorb radiation, for simultaneously passing radiation within the two non-overlapping pass bands, said dual pass band filter means located between the sample chamber and the radiating element of said differential temperature source means;

said differential temperature source means and said dual pass band filter means remaining stationary when the gas analyzer is in use.

4. A gas analyzer for determining the concentration of a gas that is included in a sample, comprising in combination:

a sample chamber containing the sample;

differential temperature source means including a radiating element and including means for altering the temperature of said radiating element from $T_1$ to $T_2$ and from $T_2$ to $T_1$ while the gas analyzer is in use, for producing radiation having a first spectrum when the temperature is $T_1$ and having a second spectrum when the temperature is $T_2$;

dual pass band filter means located on the opposite side of said sample chamber from the radiating element of said differential temperature source means, and having two non-overlapping pass bands, one of which is centered at a wavelength at which the gas absorbs radiation and the other of which is centered at a wavelength at which the sample does not absorb radiation, for simultaneously passing radiation within the two non-overlapping pass bands;

detector means for intercepting radiation that has passed through said dual pass band filter means and through said sample chamber and for converting the intercepted radiation to an electrical signal; and, circuit means electrically connected to said detector means for processing the electrical signal to determine the concentration of the gas;

said sample chamber, said differential temperature source means, said dual pass band filter means, said detector means, and said circuit means all remaining stationary when the gas analyzer is in use.

5. The gas analyzer of claim 4 wherein the gas is methane, wherein one of said two non-overlapping pass bands is centered at a wavelength $L_1 = 2.20$ microns and the other of which is centered at a wavelength $L_2 = 3.40$ microns.

6. In a gas analyzer of the type having a sample chamber containing a sample including a gas whose concentration is to be determined and through which radiation passes to a greater or lesser extent depending on the concentration of the gas, having a detector that intercepts radiation that has passed through the sample of gas and that converts the intercepted radiation to an electrical signal, and having circuit means connected to the detector for processing the electrical signal, the improvement comprising in combination:

differential temperature source means including a radiating element and means for altering the temperature of said radiating element from $T_1$ to $T_2$ and from $T_2$ and $T_1$ while the gas analyzer is in use, for producing radiation having a first spectrum when the temperature is $T_1$ and having a second spectrum when the temperature is $T_2$; and, dual pass band filter means having two non-overlapping pass bands, one of which is centered at a wavelength at which the gas absorbs radiation and the other of which is centered at a wavelength at which the sample does not absorb radiation, for simultaneously passing radiation within the two non-overlapping pass bands, said dual pass band filter means located between the sample chamber and the detector;

said differential temperature source means and said dual pass band filter means remaining stationary when the gas analyzer is in use.

* * * * *